United States Patent [19]
Goff et al.

[11] Patent Number: 5,560,920
[45] Date of Patent: Oct. 1, 1996

[54] CALCIUM FORMULATIONS FOR PREVENTION OF PARTURIENT HYPOCALCEMIA

[75] Inventors: Jesse P. Goff; Ronald L. Horst, both of Ames, Iowa

[73] Assignee: The United States of America, as represented by the Secretary of Agriculture, Washington, D.C.

[21] Appl. No.: 418,389

[22] Filed: Apr. 7, 1995

[51] Int. Cl.⁶ ........................................ A23K 1/00
[52] U.S. Cl. .......................... 424/438; 424/484; 424/602
[58] Field of Search ..................... 424/400, 438, 424/484, 602

[56] References Cited

U.S. PATENT DOCUMENTS

| | | | |
|---|---|---|---|
| 3,262,847 | 7/1966 | Flodin et al. | 536/112 |
| 3,461,205 | 8/1969 | Ringarp | 424/195.1 |
| 4,223,045 | 9/1980 | Fink | 426/335 |
| 4,248,734 | 2/1981 | Romero-Sierra et al. | 252/400 |
| 4,931,290 | 6/1990 | Rebhan | 424/692 |
| 5,393,535 | 2/1995 | Kjems | 424/678 |

FOREIGN PATENT DOCUMENTS 2153670  8/1985  United Kingdom.

OTHER PUBLICATIONS

Goff et al., "Calcium Salts for Treating Hypocalcemia: Carrier Effects, Acid–Base Balance, and Oral Versus Rectal Administration", Journal of Dairy Science, 77(Y), pp. 1451–1456 Apr. 1994.

Goff, J. P. and Horst, R. L., "Oral Administration of Calcium Salts for Treatment of Hypocalcemia in Cattle", Journal of Dairy Science, 76, 1993, pp. 101–108.

Jonsson, G. and Pehrson, B., "Trials with Prophylactic Treatment of Parturient Paresis", The Veterinary Record, Nov. 7, 1970, 87, pp. 574–583.

Primary Examiner—Jeffrey C. Mullis
Attorney, Agent, or Firm—M. Howard Silverstein; Curtis P. Ribando; John D. Fado

[57] ABSTRACT

Calcium propionate treatments for milk fever (parturient paresis) have been formulated (1) with propylene glycol and either citric or phosphoric acid as a non-hardening paste and (2) with sodium chloride as a liquid drench. These compositions are particularly useful for treating this hypocalcemic disorder associated with the onset of lactation in dairy cows.

6 Claims, 2 Drawing Sheets

CALCIUM FORMULATIONS FOR PREVENTION OF PARTURIENT HYPOCALCEMIA

BACKGROUND OF THE INVENTION

1. Field of the Invention

Milk fever (parturient paresis) is a hypocalcemic disorder associated with the onset of lactation in dairy cows. Hypocalcemia occurs because calcium (Ca) leaves the extracellular fluid pool to enter the mammary gland faster than it can be replaced by intestinal calcium absorption or bone calcium resorption. Milk fever can be prevented by measures that increase the rate of entry of calcium into the extracellular fluid compartment from intestine or bone.

2. Description of the Prior Art

Measures to increase the rate of calcium entry into the extracellular fluid include reduction of the calcium content [Goings, R. L. et al., "Prevention of parturient paresis by a prepartum, Ca-deficient diet", *J. Dairy Sci.*, 57:1184 (1974); Jorgensen, N. A., "Combating milk fever", *J. Dairy Sci.*, 57:933 (1974)] or the cation content of the prepartal diet [Block, E., "Manipulating dietary anions and cations for prepartum dairy cows to reduce incidence of milk fever", *J. Dairy Sci*, 67:2939 (1984); Goff, J. P. et al., "Addition of chloride to a prepartal diet high in cations increases 1,25-dihydroxyvitamin D response to hypocalcemia preventing milk fever", *J. Dairy Sci.*, 74:3863 (1991); Oetzel G. R., "Meta-analysis of nutritional risk factors for milk fever in dairy cattle", *J. Dairy Sci.*, 74:3900 (1991)], administration of parathyroid hormone [Goff, J. P. et al., "Effect of synthetic bovine parathyroid hormone in dairy cows: prevention of hypocalcemic parturient paresis", *J. Dairy Sci.*, 69:2278 (1986)] and administration of vitamin D metabolites [Bar, A. et al., "Observation on the use of 1-$\alpha$- hydroxyvitamin $D_3$ in the prevention of bovine parturient paresis: the effect of a single injection on plasma 1-$\alpha$-hydroxyvitamin $D_3$, 1,25-dihydroxyvitamin $D_3$, Ca, and hydroxyproline", *J. Dairy Sci.*, 68:1952 (1985); Goff, J. P. et al., "Effect of subcutaneously released 24F-1,25-dihydroxyvitamin $D_3$ on incidence of parturient paresis in dairy cows", *J. Dairy Sci.*, 73:406 (1990); Hoffsis, G. F. et al. "The use of 1,25-dihydroxycholecalciferol in the prevention of parturient hypocalcemia in dairy cows", *Bovine Pract.*, 13:88 (1979)]. Oral administration of $CaCl_2$ in aqueous and gel forms at parturition as a preventive of milk fever in dairy cattle has also been attempted with varying success [Hallgren, W., "Studies on parturient paresis in dairy cows", *Nord Veterinaermed.*, 7:433 (1955); Jonsson, G. et al., "Trials witch prophylactic treatment of parturient paresis", *Vet. Rec.*, 87:575 (1970); Oetzel, G. R., "Effects of prophylactic treatment with a calcium chloride gel on serum calcium concentration at calving, milk fever, and displaced abomasum in Holstein cows", *J. Dairy Sci*, 76 (supplement): 304 (1993); Queen W. G. et al., "Effects of oral administration of a Ca containing gel on serum Ca concentration in postparturient dairy cows", *J. Am. Vet. Med. Assoc.*, 202:607 (1993); Ringarp, N. et al., "The prophylaxis of milk fever in cattle by oral administration of Ca chloride gel", *Zentralbl. Veterinaermed. Reihe A* 14:242 (1967)]. Most commercially available $CaCl_2$ products are packaged in tubes containing about 50 g of calcium. Anecdotes suggest that cows often are treated with more than one tube to prevent milk fever or relapses to milk fever. Ample evidence exists to suggest that this treatment results in an increase in blood calcium levels for at least 4 to 6 h [Goff, J. P. et al., "Oral administration of Ca salts for treatment of hypocalcemia in cattle", *J. Dairy Sci.*, 76:101 (1993); Queen et al., supra], however, this treatment is not without risk. Calcium chloride is very irritating. Should abrasions exist in the cow's mouth prior to treatment, the $CaCl_2$ might irritate the exposed submucosa to the point of ulceration. Also, calcium chloride rapidly induces a metabolic acidosis in treated animals, as evidenced by the reduction in both blood and urine pH. Chloride is a fixed (non-metabolizable) anion that is readily absorbed into the blood. Blood pH decreases to maintain electroneutrality of the blood [Stewart, P. A., "Modern quantitative acid-base chemistry", *Can. J. Physiol. Pharmacol.*, 61:1444 (1983)]

Recently, Goff et al. [*J. Dairy Sci.* 76:101 (1993)], supra, established that concentrated $CaCl_2$ solutions are absorbed with greater efficiency than are dilute $CaCl_2$ solutions when administered as a drench (using increased blood calcium concentration as an indicator) and that $CaCl_2$ in solution is absorbed with greater efficiency than is $CaCl_2$ suspended in a commercial paste. Calcium chloride increased blood calcium concentrations more quickly than did calcium propionate, but calcium propionate effects lasted longer. The $CaCO_3$ drenches were ineffective. Drenching with $CaCl_2$ solutions increased blood calcium to a greater extent than did placing the solution into the rumen via stomach tube. However, a risk of aspiration of liquid drenches in hypocalcemic animals with reduced epiglottal reflex exists, making the development of a paste formulation advantageous in some circumstances. Goff et al. [*J. Dairy Sci.* 76:101 (1993)], supra, also reported that clinical metabolic acidosis had occurred in a cow treated with 100 g of calcium as $CaCl_2$ at calving and again at 12 h postcalving.

Preparations of calcium propionate do not induce a metabolic acidosis in treated cattle and are nearly as effective at raising plasma calcium concentration as $CaCl_2$ preparations. In addition, the gluconeogenic properties of propionate may be useful in reducing the incidence of ketosis and fatty liver.

Calcium-containing commercial gels can be made from water-soluble (such as propylene glycol) and water-insoluble carriers (such as vegetable oils). The oils tend to be less expensive and may be more palatable; however, studies indicate that oil-based carriers appear to decrease the availability of the calcium for absorption. It seems likely that insoluble calcium soaps are formed. On the other hand, propylene glycol can be used to form a gel that is fairly readily soluble in water and that will also serve as an energy source for the cow.

Though calcium propionate formulations demonstrate promise in terms of long-lasting physiological effects, they possess certain inherent problems related to administration. When formulated with propylene glycol into pastes, the resultant compositions tend to set into unmanageable hardened masses which are difficult to eject from tubes. Also, calcium absorption is not as rapid as when it is administered as the chloride salt. In extreme cases of hypocalcemia, the slower absorption rate could impede recovery of the animal.

SUMMARY

We have now discovered calcium propionate formulations for prophylactic treatment of milk fever which obviate the problems of paste hardening and slow rate of calcium absorption. Essentially two formulations are contemplated: (1) a paste comprising calcium propionate, propylene glycol and either citric or phosphoric acid; and (2) a liquid drench comprising calcium propionate and sodium chloride.

In accordance with this discovery, it is an object of the invention to provide novel compositions for prophylactic treatment of milk fever in post parturient mammals.

Another object of the invention is to provide an oral calcium treatment that will not be as caustic to mucosal tissues as the calcium chloride based treatments currently on the market.

A further object of the invention is the prophylactic treatment of milk fever in mammals, particularly cows, by administering novel formulations which do not induce metabolic acidosis and, therefore, maintain normal physiological pH in both the blood and urine.

It is also an object of the invention to provide a prophylactic treatment of milk fever in mammals characterized by a low risk of toxicity.

These and other objects and advantages of the invention will become readily apparent from the ensuing description.

BRIEF DESCRIPTION OF THE DRAWINGS

In FIGS. 1A and 1B, a=significantly different (P<0.5) from pretreatment. b=Significantly different (P<0.01) from pretreatment. c=Significantly different (P<.001) from pretreatment. Vertical bars indicate the standard errors of the means.

DETAILED DESCRIPTION OF THE INVENTION

Figure 1A:
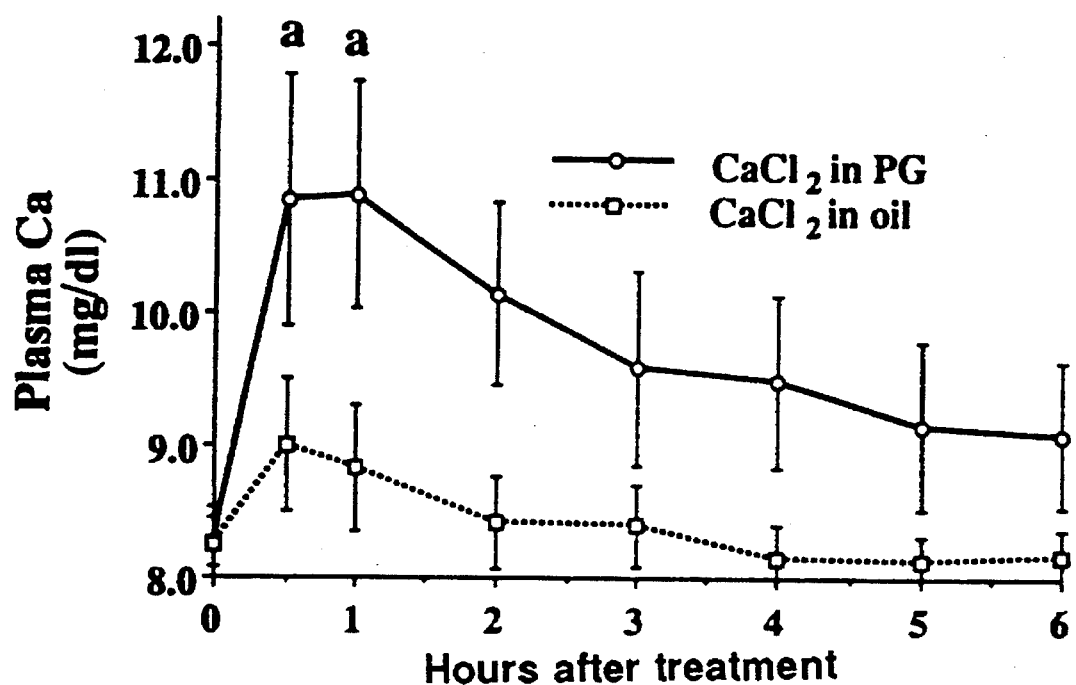
FIG. 1A is a graph of plasma calcium concentrations of cows receiving 75 g of calcium as $CaCl_2$ in a carrier based on either propylene glycol (PG) or soybean oil (oil) (n=7).

As previously stated, the compositions of the invention are formulated with calcium propionate as the basic ingredient.

In one embodiment of the invention, the calcium propionate is formulated with propylene glycol to yield a squeezable paste. The expression "squeezable paste" is defined herein to mean a gel or semi-solid which can be readily emitted from a squeeze tube, such as a toothpaste tube, or from an ejection tube, such as that which is commonly used with a caulk gun. Both the propionate and the propylene glycol serve as precursors for glucose formation. When the formulation is administered to cows, these two components provide the animal with energy and are an aid in the prevention of two other common metabolic diseases of dairy cows: ketosis and fatty liver degeneration. The propylene glycol serves a secondary purpose of imparting the desired consistency to the formulation for purposes of administration. The proportions of calcium propionate to propylene glycol would normally be in the range of about 1500–2400 g calcium propionate per liter of propylene glycol, with a preferred range of 2000–2400 g calcium propionate per liter of propylene glycol. The weight percent of calcium in calcium propionate is 21.5%.

Calcium propionate and propylene glycol, without further treatment, will tend to solidify within a matter of 24 hours. However, we have discovered that the addition of either citric acid or phosphoric acid in the amount of about 7–9% by weight of the total composition, and preferably in the amount of 7.25–7.5% by weight of the total composition, will maintain the composition as a smooth, squeezable paste for at least 2 months. These acids are also palatable to most animals, especially cows, and thereby render the formulations more acceptable to the animals. In most instances, citric acid is preferred.

The order of mixing the calcium propionate, propylene glycol, and acid ingredients is not particularly critical. Normally, the acid is mixed with water (for citric acid), or added directly to the propylene glycol, mixed well, and then the calcium propionate is slowly added to facilitate blending. The mixing can be conducted in a conventional mixer bowl, combining the components and mixing until the formulation is in the form of a smooth paste.

The preparation of calcium propionate paste containing 51.6 g elemental calcium is illustrated as follows. Citric or phosphoric acid in the amount of 22.5–30 g is mixed with 22.5 ml water. The resulting solution is then added to 105 ml propylene glycol followed by the addition of 240 g calcium propionate. The thoroughly mixed composition having a total volume of about 330 ml is loaded into tubes and will remain smooth and pliable for several months under storage in a sealed vessel.

In the second embodiment of the invention, a drench is prepared by combining the calcium propionate with sodium chloride in aqueous solution by any manner of mixing as known in the art. The concentration of calcium propionate in aqueous solution should be in the range of about 33–42 weight percent and preferably in the range of about 39–40 weight percent. The concentration of sodium chloride should be in the range of about 4–8 weight percent and preferably in the range of about 4.5–5.5 weight percent. As shown in Example 3, below, the NaCl added to the drench at these levels significantly (P<0.07) increases calcium absorption, presumably by stimulating closure of the esophageal groove. This enhances the efficacy of treatment by permitting a portion of the calcium propionate to bypass the rumen, thereby enhancing absorption. Therefore, formulations within the scope of the invention intended for administration to cows must have a level of NaCl sufficient to promote such stimulation.

As an illustration of the drench formulation preparation, 50 g NaCl are mixed with 700 ml water, and 465 g of calcium propionate powder are added slowly with stirring. The total volume is about 1165 ml. Though this slurry is susceptible to settling after about 24 hrs, it can be easily resuspended by shaking the container. The slurry can be stored for several months in a closed vessel.

Other agents and additives as well-known in the art could be included in the formulations of either of the aforementioned embodiments. For example, vitamins, minerals, salts, and coloring salts could be incorporated in relatively minor amounts. Preferably, each such additive would comprise less than about 10% by weight of the composition, and collectively, the additives would comprise no more than about 25% by weight of the composition.

As previously indicated, the calcium propionate paste would typically be administered orally from a squeeze tube or a caulk-type ejection tube. The calcium propionate drench is best administered by applying the solution between the cheek and teeth and allowing the animal to close its mouth and swallow normally. The treatments are most advantageously administered anytime within a few days prior to parturition to about 3 days after parturition. An appropriate dose of paste or drench could be readily determined by the skilled artisan in terms of the predetermined amount of calcium required for the anticipated condition of the animal being treated. Factored into the determination would be species and size of the animal, the anticipated absorption rate of the calcium administered as calcium propionate, and the anticipated calcium deficit profile during the course of treatment. For prophylactic treatment of milk fever in parturient cows, the typical dose would be in the range of about 50–150 g elemental calcium. The drench will also contain approximately about 50–75 g NaCl per treatment.

The following examples further illustrate the invention but should not be construed as limiting the invention, which is defined by the claims.

EXAMPLE 1

Calcium Salt and Carrier Comparisons

Seven adult (5- to 9-yr-old) nonpregnant, nonlactating Jersey cows were used in this example to test the effect of a water soluble carrier (propylene glycol) versus a water-insoluble carrier (soybean oil) on the ability of $CaCl_2$ and calcium propionate to increase plasma calcium concentrations. The $CaCl_2$ (Sigma, St. Louis, Mo.) and calcium propionate (Eastman Kodak, Rochester, N.Y.) were comprised of 36% and 21.5% calcium, respectively. Thus, 208 g of $CaCl_2$ or 349 g of calcium propionate provided 75 g of elemental calcium. A paste was made by adding 300 ml of either propylene glycol (Phoenix Pharmaceutical, St. Joseph, Mo.) or soybean oil (Flav-o-rite, Eden Prairie, Minn.) to 75 g of calcium as either the chloride or propionate salt. The mixture was hand-blended until a paste or emulsion formed that had a volume of approximately 500 ml. The paste was loaded into two 300-ml plastic tubes and administered by means of a caulking gun to the cow within 1 h of preparation. The $CaCl_2$ in soybean oil preparation tended to precipitate with time, and the calcium propionate in propylene glycol preparation solidified if left in the tube for more than 12 h. Each cow received one of the four preparations once each week for 4 wk in a switchback design experiment. Heparinized blood samples (10 ml) were obtained from the jugular vein before treatment and 0.5, 1, 2, 3, 4, 5, and 6 h after treatment. Plasma calcium concentration was determined by atomic absorption spectrophotometry [Perkin-Elmer Corporation. 1965. in: Analytical methods for atomic absorption spectrophotometry. Perkin-Elmer, Norwalk, Conn.].

The relative increase in plasma calcium concentration induced by treatment was considered to be proportional to the area under the curve delineated by the line graph of plasma calcium versus hours after treatment. The area under the curve was determined by graphing each cow's plasma calcium response to each treatment versus hours on the same scale, drawing a baseline equivalent to the pretreatment plasma calcium concentration, cutting the paper along the outline of the graph, and weighing the paper on a balance. The mean and standard error of the mean for areas under the curve could be determined for each treatment and are arbitrarily expressed in milligrams. Mean differences across treatments or time in the parameters measured were assessed by ANOVA. When the group means differed, the Tukey-Kramer multiple comparison test was used to compare means [Snedecor G. W. et al., Page 77 in Statistical Methods. Iowa State University Press, Ames, IA. (1967)]. Comparisons across time were made against the pretreatment calcium concentration. Statistical significance was designated at $P<0.05$ unless otherwise specified.

Figure 1B:
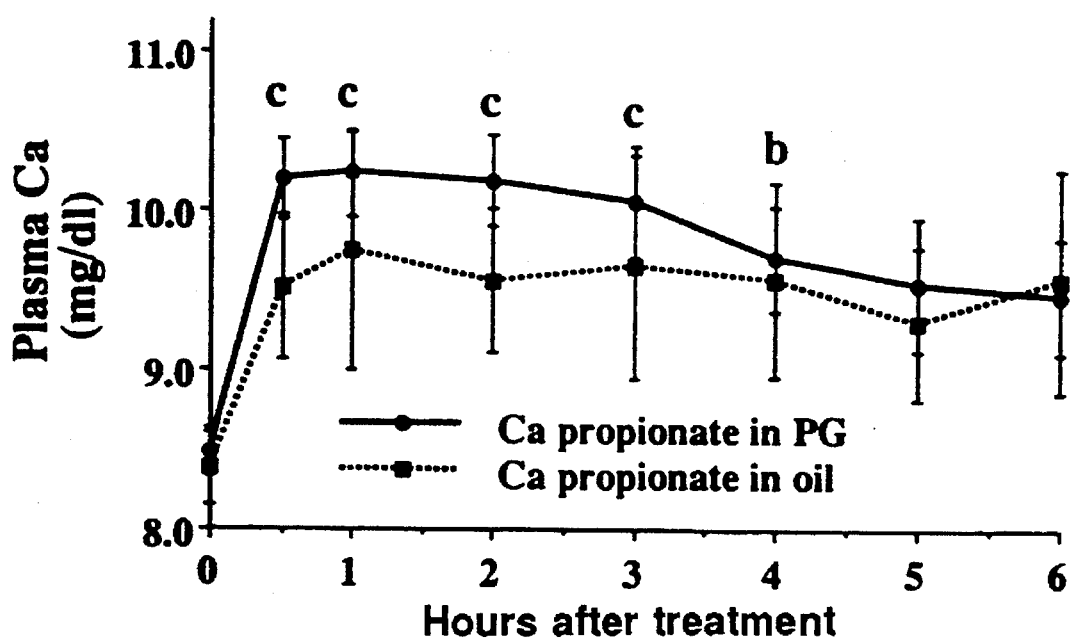
FIG. 1B is a graph of plasma calcium concentrations in cows receiving 75 g of calcium as calcium propionate in a carrier based on either propylene glycol (PG) or soybean oil (oil) (n=7).

The paste of 75 g of calcium as calcium propionate in propylene glycol did not increase plasma calcium as rapidly as the 75 g calcium as $CaCl_2$ paste (FIG. 1). However, the increase in plasma calcium was sustained for a longer period with calcium propionate. The increases in plasma calcium described by the areas under the curves delineated by the line graph of plasma calcium concentration versus hours after treatment for $CaCl_2$ and calcium propionate in propylene glycol were similar (390±150 and 350±60 mg, respectively). For cows treated with $CaCl_2$ and calcium propionate administered in soybean oil, the areas under the curves were 70±20 and 280±100 mg, respectively, and plasma calcium concentrations were not statistically increased over pretreatment concentrations at any time point (FIG. 1). Thus, vegetable oil preparations of these salts were poorly absorbed.

EXAMPLE 2

Acid-Base Effects of Oral Calcium Salts

To test the effects of calcium propionate and $CaCl_2$ on blood acid-base balance, 5 cows were treated with 75 g of calcium as either the $CaCl_2$ or calcium propionate salt mixed with propylene glycol as described in Example 1. Heparinized 3-ml jugular blood samples were obtained in glass syringes at 3 and 24 h after treatment. Blood samples were maintained at 4° C. in an ice water bath until analyzed. Analyses were by a blood gas analyzer within 1.5 h of sampling. Urine pH was determined on a sample representing urine formed between 22 and 24 h after treatment (150 pH meter; Corning, Corning, N.Y.). We obtained samples by manually stimulating micturition in the cows 22 h after treatment to empty the bladders and collecting urine upon stimulation of micturition at 24 h after treatment. This urine sample should represent urine formed by kidneys from 22 to 24 h after treatment. Urine samples were placed in ice water, and pH was determined within 1 h.

Figure 2:
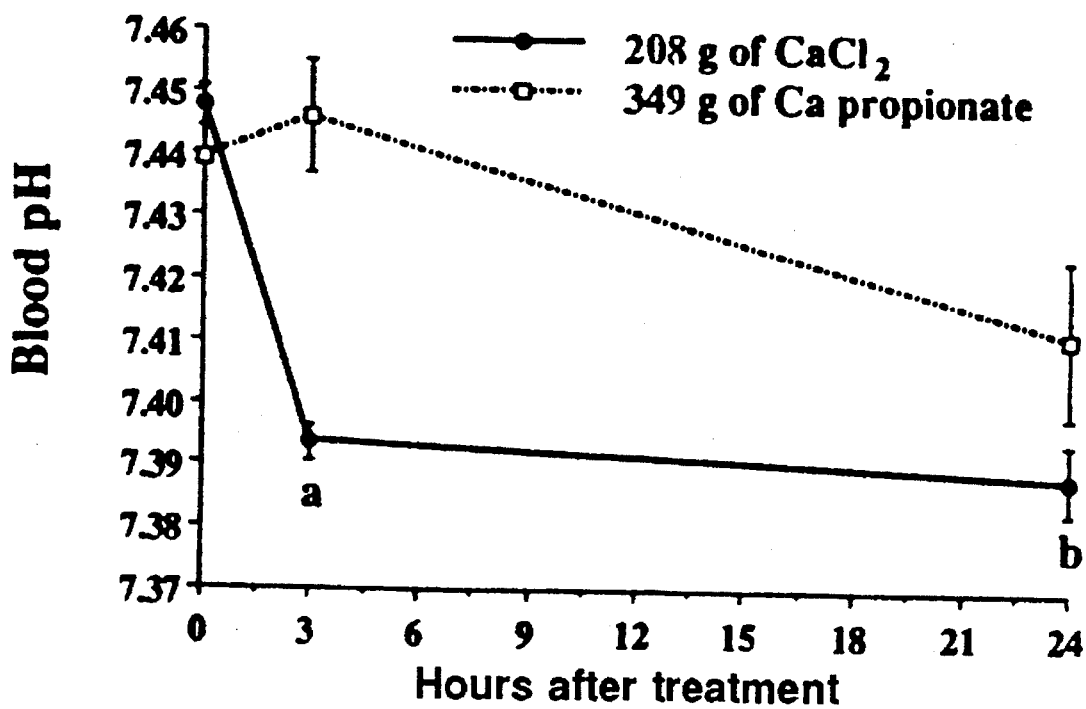
FIG. 2 is a graph of blood pH of cows receiving 75 g of calcium as either $CaCl_2$ or calcium propionate in propylene glycol carrier (n=5). a=Significantly different (P<0.01) from pretreatment. b=Significantly different (P<0.001) from pretreatment. Vertical bars indicate the standard errors of the means.

FIG. 2 depicts blood pH profiles of cows receiving 75 g of calcium as either $CaCl_2$ or calcium propionate in propylene glycol carrier. Before treatment, cows receiving $CaCl_2$ and calcium propionate had similar blood pH. In cows treated with $CaCl_2$ salts, blood pH was significantly decreased from pretreatment concentration at 3 h ($P<0.01$) and 24 h ($P<0.001$) after treatment. Blood pH did not change from pretreatment in cows treated with the calcium propionate preparation. The pH of urine formed between 22 and 24 h after treatment was significantly different ($P<0.001$); 6.25±0.19 for cows treated with $CaCl_2$ and 8.35±0.08 for cows treated with calcium propionate.

EXAMPLE 3

Calcium propionate—sodium chloride drench

Figure 3:
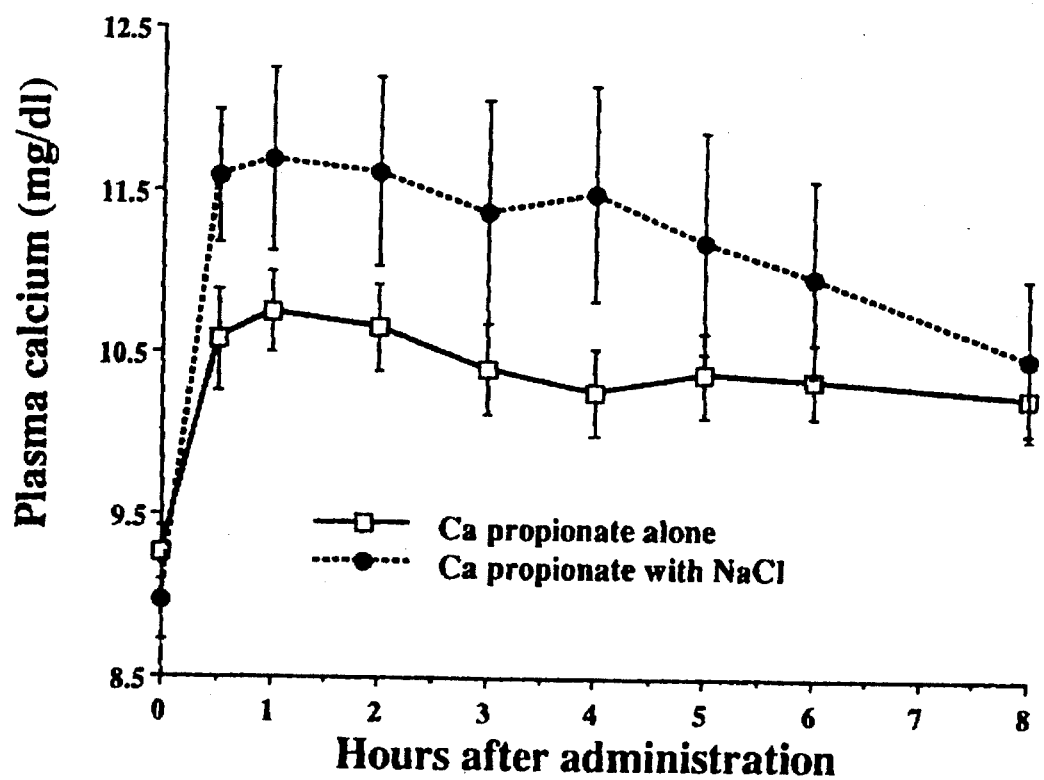
FIG. 3 is a graph of plasma calcium concentrations in 12 cows drenched with 442 g calcium propionate preparation with or without 50 g NaCl added to the preparation. Vertical bars indicate the standard errors of the means.

The efficacy of including NaCl in a calcium propionate drench was established in the following experiment. Twelve Jersey cows (non-lactating, non-pregnant) were treated at time 0 with a drench containing 442 g calcium propionate in 700 ml water (total volume of 1200 ml), with 0 or 50 g NaCl added to the preparation. All 12 cows received both treatments in a switchback experimental design. Blood samples were obtained at 0, 0.5, 1, 2, 3, 4, 5, 6 and 8 hrs after treatment to monitor changes in plasma calcium concentration (FIG. 3).

Inclusion of NaCl into the drench preparation significantly ($P<0.05$) increased the plasma calcium concentration achieved by the calcium propionate drench.

We claim:

1. A formulation for prophylactic treatment of milk fever comprising calcium propionate and propylene glycol in proportions which form a paste, wherein said formulation further comprises an acid selected from the group consisting of citric acid and phosphoric acid, wherein the amount of the acid is effective to stabilize an otherwise unstable paste.

2. A formulation as described in claim 1, wherein the amount of the acid is in the range of about 7–9% by weight.

3. A formulation as described in claim 2, wherein the amount of calcium propionate is about 1500–2400 g per liter propylene glycol.

4. A method for prophylactic treatment of milk fever in a mammal comprising orally administering to said mammal an effective amount of the formulation of claim 1.

5. A method of making a formulation comprising calcium propionate and propylene glycol in the form of a stable paste comprising the step of adding to said formulation an amount of an acid effective to stabilize an otherwise unstable paste selected from the group consisting of citric acid and phosphoric acid.

6. A method as described in claim 5, wherein the effective amount of acid is within the range of 7–9% by weight of the formulation.

* * * * *